United States Patent [19]
Richards et al.

[11] Patent Number: 5,093,364
[45] Date of Patent: Mar. 3, 1992

[54] 5-FLUOROANTHRANILIC FUNGICIDES

[75] Inventors: Ian C. Richards, Haverhill; Brian J. Wright, Cambridge; John H. Parsons, Saffron Walden; Alister C. Baillie, Bottisham, all of England

[73] Assignee: Schering Agrochemicals Limited, England

[21] Appl. No.: 397,726

[22] Filed: Aug. 23, 1989

[30] Foreign Application Priority Data

Aug. 24, 1988 [GB] United Kingdom ............... 8820129

[51] Int. Cl.$^5$ .................... A01N 33/06; A01N 43/84
[52] U.S. Cl. ................................. 514/533; 514/563; 514/564; 514/567; 514/230.5
[58] Field of Search ............ 562/442; 514/568, 230.5, 514/567, 533, 563, 564; 544/92

[56] References Cited

U.S. PATENT DOCUMENTS

| | | | |
|---|---|---|---|
| Re. 32,087 | 2/1986 | Hamprecht et al. | 544/92 |
| 2,568,142 | 9/1951 | Bruce et al. | 562/442 |
| 3,462,533 | 8/1969 | Irikura et al. | 514/521 |
| 3,631,105 | 12/1971 | Bell et al. | 562/442 |
| 3,657,436 | 4/1972 | Berger et al. | 514/568 |
| 4,673,740 | 6/1987 | Hamprecht et al. | 544/92 |

FOREIGN PATENT DOCUMENTS 2241012  3/1973  Fed. Rep. of Germany .
2111975  7/1983  United Kingdom .

OTHER PUBLICATIONS

Krantz et al., J. Med. Chem. 1990, 33, 464-79.

*Primary Examiner*—Mukund J. Shah
*Assistant Examiner*—E. C. Ward
*Attorney, Agent, or Firm*—Ostrolenk, Faber, Gerb & Soffen

[57] ABSTRACT

Compounds of formula I

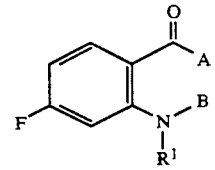

where A is OH, B is H, $C_{1-4}$ alkyl optionally substituted by $C_{1-4}$ alkoxy carbonyl, $C_{2-4}$ alkenyl, $CONR_2$ or $COR_4$ $R_1$ is H, $R_2$ is $C_{1-4}$ alkyl, and $R_4$ is $C_{1-4}$ alkyl, or phenyl, optionally substituted by carboxy have pesticidal and especially fungicidal activity. Many of the compounds are novel and these compounds per se, form part of the invention.

14 Claims, No Drawings

5-FLUOROANTHRANILIC FUNGICIDES

This invention relates to compounds having pesticidal and especially fungicidal activity.

3,1-Benzoxazin-4-ones, which can be considered as ring-closed derivatives of anthranilic acids, have been disclosed as having pesticidal activity (e.g. DE 2241012 and EP 17 931) but none of these describe 7-fluoro substituted compounds. It will be appreciated that the 7-position on the 3,1-benzoxazin-4-one ring corresponds to the 4-position of the "parent" anthranilic acid. Certain 7-fluoro substituted quinolones have been disclosed as having pharmaceutical activity (e.g. EP 135 367, GB 2047691 and 2111975) but no agricultural uses are described for these compounds. 4-Fluoroanthranilic acid itself and certain other derivatives are known but we are not aware that any agricultural pesticidal use has been disclosed for these compounds. We have now found that 4-fluroanthranilic acid and certain derivatives have pesticidal activity and especially activity against phytopathogenic fungi.

Thus, according to the invention there is provided a pesticidal composition which comprises a compound of formula I

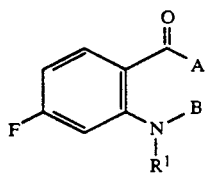

where
R$^1$ is hydrogen, optionally substituted alkyl, cycloalkyl, alkenyl or alkynyl;
and either
(i) A is hydroxy, XR$^2$, NR$^3$R$^4$ or NHNR$^3$R$^4$, and
   a) B is hydrogen, alkyl, cycloalkyl, alkenyl or alkynyl, each of which is optionally substituted, non-aromatic heterocyclyl or the group COR$^4$, COOR$^2$, CXNR$^2$R$^3$, SO$_2$R$^2$, SO$_2$NR$^5$R$^6$, PX(OR$^2$)$_2$ or PX(NR$^5$R$^6$)$_2$, or
   b) B and R$^1$ together represent =CR$^2$R$^3$, where R$^2$ and R$^3$ are as defined below or together are alkylene; or
(ii) A and B together with the atoms to which they are attached can form a ring, in which case R can also represent a bond between the nitrogen to which it is attached and B;
R$^2$ is alkyl, cycloalkyl, alkenyl or alkynyl, each of which is optionally substituted, or is aryl or a non-aromatic heterocyclyl group;
R$^3$ is hydrogen, alkyl, cycloalkyl, alkenyl or alkynyl, each of which is optionally substituted, or is —SO$_2$R$^4$;
R$^4$ has the same meaning as R$^2$ or is hydrogen;
R$^5$ and R$^6$ are the same or different optionally substituted alkyl or alkenyl groups;
X is oxygen or sulphur;
and where —NR$^2$R$^3$, —NR$^3$R$^4$ and —NR$^5$R$^6$ can form a ring; and agriculturally acceptable salts with an organic or inorganic base of any compound which is an acid or with an organic or inorganic acid of any compound which is a base; said compound being in admixture with an agriculturally acceptable diluent or carrier.

Alkyl groups are preferably of 1 to 4 carbon atoms, especially methyl. Alkenyl and alkynyl groups are preferably of 2 to 4 carbon atoms. Cycloalkyl groups are preferably of 3 to 8 carbon atoms. Substituents, when present on any alkyl, cycloalkyl, alkenyl or alkynyl group, include halogen, alkoxy (e.g. of 1 to 4 carbon atoms), haloalkoxy, hydroxy, alkylthio, nitro, optionally substituted amino, carboxy, alkoxycarbonyl, acyloxy, aryl and trialkylsilyl. Cycloalkyl groups may also be substituted by alkyl. Aryl groups are usually phenyl, optionally substituted, e.g. by halogen, alkyl, haloalkyl, alkoxy, optionally substituted amino or nitro. The term aryl may include heteroaryl groups. The terms heteroaryl and heterocyclyl include groups such as thienyl, furyl, pyridyl, pyrimidinyl, pyrazolyl, thiazolyl, thiazolinyl, thiazolidinyl, oxazolyl, benzimidazolyl, tetrazolyl, benzoxazolyl, thiadiazolyl, dioxolanyl, imidazopyridinyl, 1,3-benzoxazinyl, 1,3-benzothiazinyl, oxazolopyridinyl, tetrahydropyranyl, triazolyl, triazinyl, imidazolyl, morpholino, benzofuranyl, pyrazolinyl, quinolinyl, quinazolinyl, dihydroquinazolinyl or benzothiazolyl, which themselves may be substituted, e.g. as for phenyl. The term acyl includes the residue of sulphonic and phosphorus containing acids as well as carboxylic acids. Acyl groups are preferably alkanoyl, e.g. of 1 to 4 carbon atoms. Amino groups may be substituted, e.g. by one or two alkyl groups or two substituents can form a ring, e.g. morpholine or piperidine.

When —NR$^2$R$^3$, —NR$^3$R$^4$ and —NR$^5$R$^6$ form a ring this is generally a 5 to 7 membered ring which may be substituted and may contain other hetero atoms, e.g. morpholine, thiomorpholine, piperidine or imidazole.

When A and B form part of a ring this is generally a 5 or 6 membered ring which besides the nitrogen can contain other hetero atoms, such as nitrogen, oxygen, phosphorus or sulphur, and can be further substituted. R$^1$ can represent a bond between the nitrogen atom and the adjacent atom which is not part of the fused benzo ring. Examples of compounds of formula of this type are

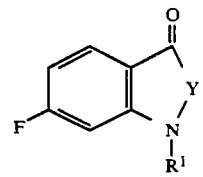

where Y is

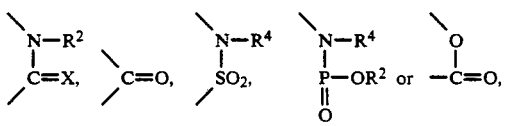

or

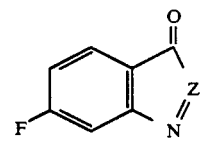

where Z is

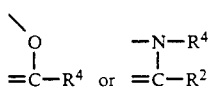

Many of the compounds of formula I are novel and the invention thus include all such novel compounds and especially those where the groups are defined above with the proviso (i) when A is hydroxy or alkoxy and $R^1$ is hydrogen, then B is not hydrogen or acetyl, (ii) when $R^1$ is hydrogen and if A and B form a ring then it is not one in which the group Y is CO or COO, (iii) when A is alkoxy and $R^1$ is hydrogen, then B is not methyl, or (iv) if A and B form a ring then it is not a 4-quinolone ring.

Some novel compounds of formula I have weak pesticidal activity but still have utility as intermediates and such compounds also form one aspect of the invention.

The compounds of the invention have activity as fungicides, especially against soil-borne fungal diseases of plants, e.g. *Rhizoctonia solani* and *Pythium ultimum*. They may however have activity against other fungi, for example e.g. vine downy mildew (*Plasmopara viticola*), rice sheath blight (*Pellicularia sasakii*), grey mould (*Botrytis cinerea*), and apple scab (*Venturia inaequalis*). Other fungi against which the compounds may be active include other general pathogens of Deuteromycete, Ascomycete, Phycomycete or Basidiomycete origin.

Some of the compounds also have other pesticidal activity, especially herbicidal and insecticidal activity.

The invention thus also provides a method of combating pests, and especially fungi, particularly soil-borne fungi at a locus infested or liable to be infested therewith, which comprises applying to the pest or its locus a compound of formula I.

The composition of the invention may of course include more than one compound of the invention.

In addition the composition can comprise one or more additional active ingredients, for example compounds known to possess plant-growth regulant, herbicidal, fungicidal, insecticidal or acaricidal properties. Alternatively the compounds of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to the target locus is preferably within the range of 0.01 to 3.0 per cent by weight, especially 0.01 to 1.0 per cent by weight. In a primary composition the amount of active ingredient can vary widely and can be, for example, from 5 to 95 per cent by weight of the composition.

In the method of the invention the compound is generally applied to seeds, plants or their habitat. Thus the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.05 to 20 kg per hectare, more preferably from 0.1 to 10 kg per hectare.

The compounds of the invention may be prepared in a variety of ways for example as shown in the following reaction schemes. Methods will also be apparent from the various Examples.

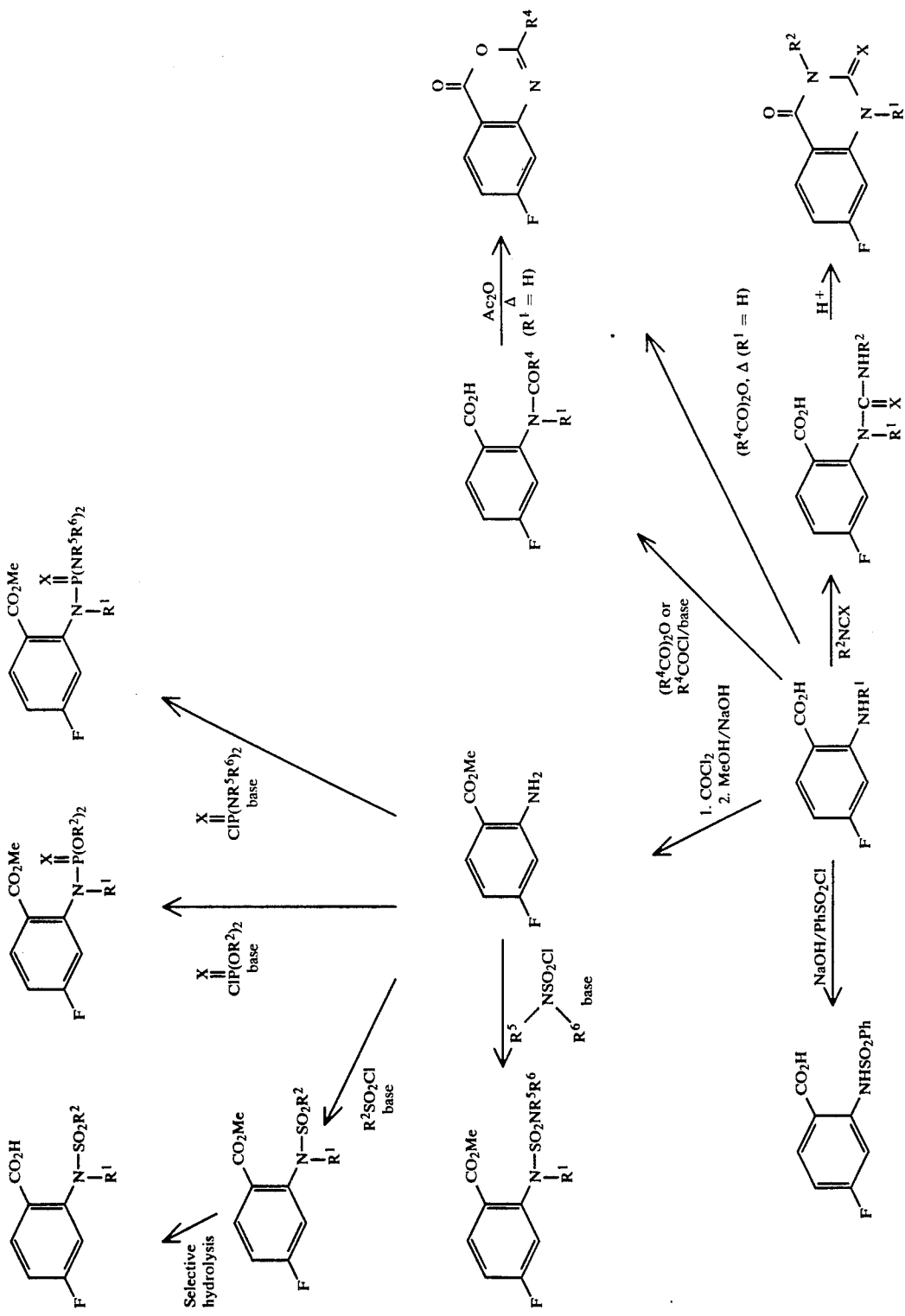

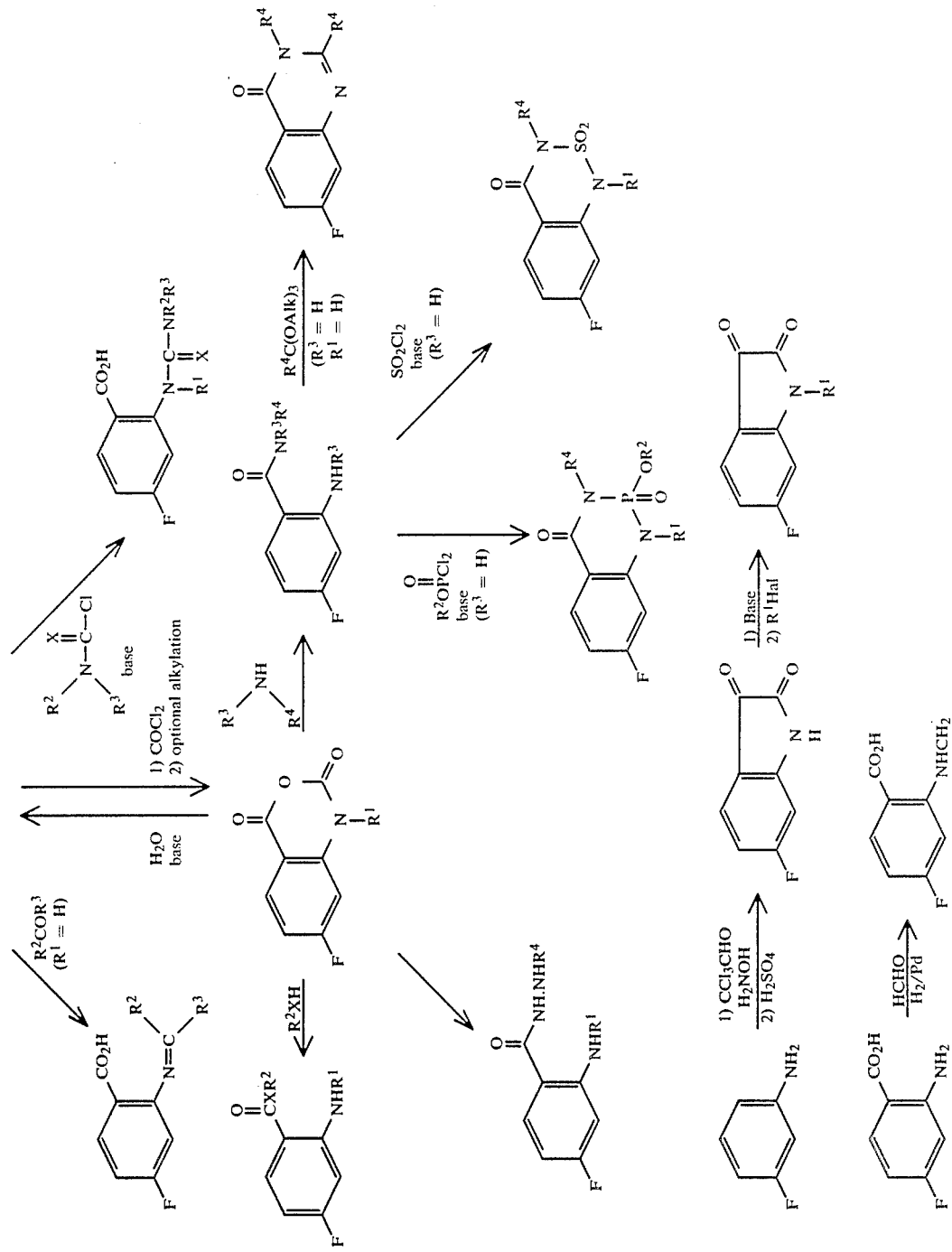

The invention is illustrated in the following Examples. Structures of isolated novel compounds were confirmed by elemental and/or other appropriate analyses. Temperatures are in °C.

EXAMPLE 1

A mixture of phthalic anhydride (4.8 g) and 4-fluoroanthranilic acid (5 g) in dichloromethane (100 ml) was stirred at room temperature for 48 hours and the solid collected and washed with dichloromethane to give N-(2-carboxybenzoyl)-4-fluoroanthranilic acid, m.p. 187°-188°. (Compound 1).

EXAMPLE 2

A mixture of acetyl chloride (4.6 ml) and 4-fluoroanthranilic acid (5 g) in acetic anhydride (100 ml) was heated under reflux for 48 hours, cooled and filtered. The filtrate was added to ice/water, stirred for 1 hour and extracted with ethyl acetate. The extract was dried and the solvent removed under reduced pressure to give 7-fluoro-2-methyl-3,1-benzoxazin-4-one, m.p. 159°-160°. (Compound 2).

EXAMPLE 3

Sodium hydroxide (2 pellets; approx 0.15 g) was added to a mixture of phenol (1.08 g) and 7-fluoro-1$\underline{H}$-3,1-benzoxazine-2,4-dione (2 g) followed by tetrahydrofuran (4 ml). The mixture was heated on a steam bath until gas evolution ceased. It was then cooled, diluted with ethyl acetate (100 ml), the liquid collected and washed with aqueous sodium carbonate, dried, treated with charcoal and evaporated. The crude product was recrystallised from diisopropyl ether/light petroleum to give phenyl 4-fluoroanthranilate, m.p. 69°-70°. (Compound 3).

EXAMPLE 4

A solution of aniline (1.77 g) in acetic acid (50 ml) was added to a solution of 7-fluoro-1$\underline{H}$-3,1-benzoxazine-2,4-dione (1 g) in acetic acid (100 ml) and the mixture heated at 100° for 20 minutes. It was then poured into water and the precipitate collected, dried and recrystallised from toluene to give $N^1$-phenyl-4-fluoroanthranilamide, m.p. 120°-122°. (Compound 4).

EXAMPLE 5

A solution of phenyl isocyanate (2.98 g) in toluene (30 ml) was added dropwise to a stirred suspension of 4-fluoroanthranilic acid (3.88 g) in toluene (80 ml) at 50°. The mixture was stirred at 90° for 2 hours and the toluene evaporated under reduced pressure (30 ml). The residue was recrystallised from hexane/ethyl acetate to give 4-fluoro-N-phenylcarbamoylanthranilic acid, m.p. 163°-166°. (Compound 5).

EXAMPLE 6

A mixture of the product of Example 5 (2 g) and polyphosphoric acid (150 g) was heated at 150° for 5 hours. It was then added to ice, and extracted with ethyl acetate. The extract was dried, the solvent removed under reduced pressure and the product recrystallised from aqueous ethanol to give 7-fluoro-3-phenylquinazoline-2,4-(1H,3H)-dione, m.p. 304°-306°. (Compound 6).

EXAMPLE 7

A mixture of 4-fluoroanthranilic acid (2 g), aqueous formaldehyde (37–40% w/v; 6.5 ml) and palladium on charcoal (1 g of 5%) in acetic acid (70 ml) was hydrogenated over 18 hours during which 570 ml hydrogen was taken up. The mixture was filtered, evaporated under reduced pressure and the residue recrystallised from toluene to give 4-fluoro-N-methylanthranilic acid, m.p. 180°-181°. (Compound 7)

EXAMPLE 8

A mixture of 7-fluoro-1$\underline{H}$-3,1-benzoxazine-2,4-dione (13.5 g) and sodium methoxide (0.2 g) in methanol (30 ml), was heated on a steam bath until vigorous bubbling ceased. It was then heated under reflux for 3½ hours, cooled, added to aqueous sodium bicarbonate (10%; 300 ml) and extracted with ethyl acetate. The extract was washed with water dried and evaporated to give methyl 4-fluoroanthranilate, mp 68°-70°. (Compound 8).

EXAMPLE 9

Propionyl chloride (1.7 ml) was added to a solution of 4-fluoroanthranilic acid (1 g) and triethylamine (2.8 ml) in 1,4-dioxane (30 ml). The mixture was heated under reflux for 4 hours, cooled and concentrated under reduced pressure. The residue was suspended in ethyl acetate and extracted with water. The organic phase was dried and evaporated and the residue purified by silica gel chromatography to give 4-fluoro-N-propionylanthranilic acid, mp 170°-171°. (Compound 9).

EXAMPLE 10

Methyl chloroformate (1.22 g was added dropwise at −3° to 1° (ice bath cooling) to a stirred solution of 4-fluoroanthranilic acid (2 g) and triethylamine (1.31 g) in dry tetrahydrofuran (30 ml). The mixture was then stirred at room temperature for 18 hours. The reaction mixture was diluted with ice-water and extracted with ethyl acetate.

The extract was washed with dilute hydrochloric acid, then with water and dried. Evaporation of the solvent gave a solid residue which was recrystallised from 1:1 ethyl acetate: hexane to give 4-fluoro-N-(methoxycarbonyl)-anthranilic acid, mp 161.5°-162.5°. (Compound 10).

EXAMPLE 11

Sodium hydride (80% in oil; 1.2 g) was added slowly to a stirred suspension of 7-fluoro-1$\underline{H}$-3,1-benzoxazine-2,4-dione (7 g). Effervescence occurred and a clear solution was produced. Ethyl bromoacetate (4.5 ml) was added and the mixture was stirred at room temperature for 18 hours. The solvent was evaporated and the residue was diluted with water. The solid (9.5 g) was filtered off and washed with water and hexane and dried. This solid (5.4 g) was added to a solution of sodium carbonate (5.3 g) in water (60 ml). After stirring for 6 hours the undissolved solid was filtered off. The filtrate was acidified with dilute hydrochloric acid and extracted with ethyl acetate. The extract was washed with water, dried and evaporated. The solid was purified by flash chromatography and recrystallised from diisopropyl ether to give 4-fluoro-N-(ethoxycarbonylmethyl)-anthranilic acid, mp. 123°-125°. (Compound 11).

EXAMPLE 12

Compound 11 (2.3 g) was stirred with 1N sodium hydroxide (60 ml) for 24 hours. The solution was acidified to pH 4 with hydrochloric acid and the precipitated solid was filtered off, washed with a small amount of water and dried. Recrystallisation from ethyl acetate - hexane gave 4-fluoro-N-(carboxymethyl)anthranilic acid, mp. 210° (dec.) (Compound 12).

EXAMPLE 13

4-Fluoroanthranilic acid (1.0 g) and 4-methylbenzaldehyde (0.77 g) were added to ethanol (100 ml). The mixture was heated under reflux for 6 hours, cooled and evaporated under reduced pressure. The residue was recrystallised from toluene to give 4-fluoro-N-(4-methylbenzylidene)-anthranilic acid, mp 144°-5°. (Compound 13).

EXAMPLE 14

4-Fluoroanthranilic acid (1.5 g) and sodium hydroxide (0.4 g) were stirred in cold water (100 ml) at ca. 5°. Benzenesulphonyl chloride (1.25 ml) was added and the mixture was stirred overnight, acidified and extracted with dichloromethane. The extracts were washed, dried and evaporated to give 4-fluoro-N-(phenylsulphonyl)anthranilic acid, mp 158°-9°. (Compound 14).

EXAMPLE 15

Sodium hydride (1.2 g of 80% suspension in oil) was added to a suspension of 7-fluoro-1H-3,1-benzoxazine-2,4-dione (7 g) in dimethylformamide (50 ml). After evolution of hydrogen had ceased, ethyl bromoacetate (4.5.ml) was added which caused an exothermic reaction and eventually a clear solution. After 18 hours, the solution was concentrated and water added. The resulting white solid was collected, washed with water and light petroleum and dried. The product was recrystallised from ethyl acetate/ diisopropyl ether to give 1-(ethoxycarbonylmethyl)-7-fluoro-1H-3,1-benzoxanine-2,4-dione, mp 167°-168°. (Compound 15).

EXAMPLE 16

Sodium hydride (80% in oil; 0.36 g) was added portionwise to a stirred solution of 6-fluoro-1H-indole-2,3-dione (2 g) in dry dimethylformamide (25 ml). After effervescence had ceased, ethyl bromoacetate (2 g) was added dropwise at 25° to the stirred solution. The orange mixture was stirred at room temperature for 18 hours and then poured into ice-water. The precipitated solid was filtered off, washed with water and dried. 1-(ethoxycarbonylmethyl)-1H-indole-2,3-dione, mp 168°-169°. (Compound 16).

EXAMPLE 17

4-Fluoroanthranilic acid (2 g) was added portionwise to trifluoroacetic anhydride (16 ml). After stirring and refluxing for 4 hours, the mixture was cooled and excess trifluoroacetic anhydride was removed by evaporation under reduced pressure. The resultant light brown solid was stirred at room temperature with a mixture of tetrahydrofuran (50 ml) and water (10 ml) for 18 hours. Solvent was removed by evaporation under reduced pressure to give a white solid. Recrystallisation from toluene gave 4-fluoro-N-(trifluoroacetyl)anthranilic acid, mp 166°-167.5°. (Compound 17).

EXAMPLE 18

A solution of methyl 4-fluoroanthranilate (1.8 g) 3,4-dihydro-2H-pyran (0.9 g) and pyridinium tosylate (0.1 g) in dichloromethane (20 ml) was left standing at 20° for 4 days. This solution was then washed with water (10 ml), dried with magnesium sulphate and evaporated. Column chromatography on silica gel, using diethyl ether as eluent, followed by recrystallisation of the product from ethyl acetate/diisopropyl ether gave methyl 4-fluoro-N-(tetrahydropyran-2-yl) anthranilate, mp 44°-45°. (Compound 18).

EXAMPLE 19

Methanesulphonyl chloride (0.68 g) was added dropwise to a stirred solution of methyl 4-fluoroanthranilate (1 g) in pyridine (dried over 4A sieves, 10 ml) at 0°-5°. After 18 hours at room temperature, the mixture was cooled to 0°-5° and further methanesulphonyl chloride (0.68 g) was added dropwise. The mixture was stirred for 24 hours at room temperature. Aqueous work up and recrystallisation from ethanol gave methyl N-(methylsulphonyl)-4-fluoroanthranilate, mp 115.5°-116.5°. (Compound 19).

EXAMPLE 20

7-Fluoro-1H-3,1-benzoxazine-2,4-dione (2.0 g), sodium hydroxide (0.05 g) and 2-(trimethylsilyl)ethanol (1.31 g) were heated together at 100° for 30 minutes until effervescence ceased. After cooling, the residue was suspended in diisopropyl ether, then filtered and evaporated. The residue was recrystallised from petroleum ether to give 2-(trimethylsilyl)ethyl 4-fluoroanthranilate, mp 43°-44°. (Compound 20).

EXAMPLE 21

Sodium hydride (0.41 g of 80% suspension in oil) was added to a solution of 7-fluoro-1H-3,1-benzoxazine-2,4-dione (2.5 g) in dimethylformamide (30 ml). The mixture was cooled to keep the temperature below 30° and then stirred for 1 hour until a clear solution was obtained. A solution of allyl bromide (1.2 ml) in dimethylformamide (30 ml) was added dropwise with cooling and the mixture stirred at room temperature overnight. The mixture was poured into water and extracted with dichloromethane. The extract was washed with water, dried and evaporated and the residue added to aqueous sodium carbonate (10%; 20 ml) and stirred for 3 hours, acidified with hydrochloric acid to pH 3, filtered and the solid washed with water and dried to give N-allyl-4-fluoroanthranilic acid, mp 136°-139°. (Compound 21).

Compound 7 was also prepared using the method of this Example.

EXAMPLE 22

In a similar manner to one of the processes disclosed in the previous Examples, the following were obtained

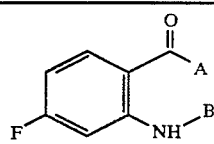

| Cpd | A | B | m.p. (°) |
|---|---|---|---|
| 22 | (4-NO$_2$—Ph)—O | H | 159-160 |
| 23 | (4-MeO—Ph)—O | H | 97-8 |
| 24 | (4-COOH—Ph)—O | H | >250 |
| 25 | (3-F—Ph)—NH | H | 126-8 |
| 26 | (EtO$_2$C)$_2$CH—NH | H | 134-5 |
| 27 | OH | COPh | 206-7 |
| 28 | OH | CH$_2$COOPr$^i$ | 192-3 |
| 29 | OH | CH$_2$COOMe | 170-171.5 |
| 30 | OH | CH$_2$CONHEt | 228-230 |
| 31 | OH | COCCl$_3$ | 214-215.5 |

-continued

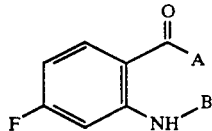

| Cpd | A | B | m.p. (°) |
|---|---|---|---|
| 32 | OMe | CH₂COOEt | 64-7 |

The following were also obtained:
a) 7-fluoro-2-phenyl-3,1-benzoxazin-4-one, m.p. 140°-142°. (Compound 33)
b) 7-fluoro-2-ethyl-3,1-benzoxazine-4-one, m.p. 107°-109°. (Compound 34)
c) 1-(isopropoxycarbonylmethyl)-7-fluoro-1H-3,1-benzoxazine-2,4-dione, mp 163°-164° (Compound 35)
d) methyl 4-fluoro-N-(2,2,2-trichloroethylidene)-anthranilic acid. (compound 36) c) 1-(ethylcarbamoylmethyl)-7-fluoro-1H-3,1-benzoxazine-2,4-dione, mp 202°-203° (Compound 37)

TEST EXAMPLE

Compounds are assessed for activity against one or more of the following fungi:
a) Foliar tests
Plasmopara viticola: vine downy mildew (PV)
Pellicularia sasakii: rice sheath blight (PS)
Botrytis cinerea: grey mould of tomato (BC)
Venturia inaequalis: apple scab (VI)

Aqueous solutions of dispersions of the compounds at the desired concentration, including a wetting agent, were applied by spray or by drenching the stem base of the test plants. These plants were then inoculated with appropriate test pathogens and kept under controlled environment conditions suitable for maintaining plant growth and development of the disease. After an appropriate time, the degree of infection of the leaf surface was visually estimated. Compounds were considered active if they gave greater than 50% control of the disease at a concentration of 125 ppm (w/v) or less.

b) Soil pathogen test
Rhizoctonia solani (RS)
Pythium ultimum (PU)

Flasks containing maize meal/sand were inoculated with the test fungus and then incubated. The maize meal/sand cultures were used to infest potting compost which was then put into plastic pots. Aqueous solutions or dispersions of the compounds, including a wetting agent, were added to the pots to give a desired concentration of compound in each pot. Control pots were set up by adding similar solutions or dispersions without the test compound. Immediately after application of the test compound each pot was sown with a number of cabbage or cotton seeds. The seeds are covered with the treated infested soil and the pots incubated at 22° C. under humid conditions for 6-21 days depending on crop. The number of emerged seedlings is counted and percentage disease control calculated by comparison with the untreated infested pots. Compounds are considered active if they give greater than 50% control of the disease at a concentration of 100 parts by weight of compound or less per million parts by volume of soil.

The following known compounds were also tested:
Compound A: 4-fluoroanthranilic acid
Compound B: N-acetyl-4-fluoroanthranilic acid
Compound C: 7-fluoro-1H-3,1-benzoxazine-2,4-dione
Compound D: 6-fluoro-1H-indole-2,3-dione
Compound E: methyl 4-fluoro-N-methylanthranilate
Activities were demonstrated as follows (+ =active).

| Compound No | PV | PS | BC | VI | RS | PU |
|---|---|---|---|---|---|---|
| 1 |  |  |  |  | + |  |
| 2 |  |  |  |  | + |  |
| 3 |  |  |  |  | + |  |
| 7 |  |  |  |  | + |  |
| 8 |  |  |  | + |  |  |
| 9 |  |  |  |  | + |  |
| 11 |  |  |  |  | + |  |
| 12 |  |  |  | + |  |  |
| 13 |  |  |  |  | + |  |
| 15 | + |  |  |  |  |  |
| 23 |  |  |  |  | + |  |
| 24 |  |  |  |  | + |  |
| 25 |  |  |  |  | + |  |
| 27 |  |  |  | + |  |  |
| 28 |  |  | + |  |  |  |
| 33 |  |  |  | + |  |  |
| 34 |  | + |  |  |  |  |
| A |  |  |  |  | + | + |
| B |  |  |  |  | + | + |
| C |  |  |  |  | + |  |
| D |  |  |  |  | + |  |

We claim:
1. A fungicidal composition which comprises a compound of formula I

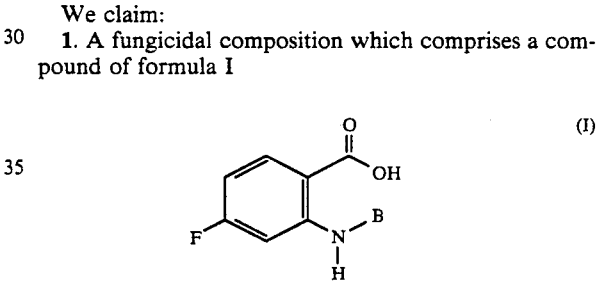

where
B is hydrogen, $C_{1-4}$-alkyl optionally substituted by $C_{1-4}$-alkoxycarbonyl, $C_{2-4}$-alkenyl, CONHR² or COR⁴,
R² is $C_{1-4}$-alkyl, and
R⁴ is $C_{1-4}$-alkyl or phenyl, optionally substituted by carboxy, said compound being in admixture with an agriculturally acceptable diluent or carrier.

2. The fungicidal composition of claim 1 in which B is propionyl.
3. The fungicidal composition of claim 1 in which B is CONHC₂H₅.
4. The fungicidal composition of claim 1 in which B is hydrogen.
5. The fungicidal composition of claim 1 in which B is optionally substituted methyl.
6. The fungicidal composition of claim 5 in which B is substituted methyl.
7. The fungicidal composition of claim 1 in which B is methoxycarbonylmethyl.
8. A method of combatting of fungi at a locus infested or liable to be infested therewith which comprises applying to the fungus or its locus a compound of formula I as defined in claim 1.
9. A method of combatting of fungi at a locus infested or liable to be infested therewith which comprises applying to the fungus or its locus a compound of formula I as defined in claim 2.

10. A method of combatting of fungi at a locus infested or liable to be infested therewith which comprises applying to the fungus or its locus a compound of formula I as defined in claim 3.

11. A method of combatting of fungi at a locus infested or liable to be infested therewith which comprises applying to the fungus or its locus a compound of formula I as defined in claim 4.

12. A method of combatting of fungi at a locus infested or liable to be infested therewith which comprises applying to the fungus or its locus a compound of formula I as defined in claim 5.

13. A method of combatting of fungi at a locus infested or liable to be infested therewith which comprises applying to the fungus or its locus a compound of formula I as defined in claim 6.

14. A method of combatting of fungi at a locus infested or liable to be infested therewith which comprises applying to the fungus or its locus a compound of formula I as defined in claim 7.

* * * * *